United States Patent
Krzewinski

[11] 3,952,738
[45] Apr. 27, 1976

[54] FOLDED SURGICAL DRAPE

[75] Inventor: Henrietta K. Krzewinski, Old Bridge, N.J.

[73] Assignee: Johnson & Johnson, New Brunswick, N.J.

[22] Filed: Jan. 29, 1975

[21] Appl. No.: 545,289

[52] U.S. Cl. .......................................... 128/132 D
[51] Int. Cl.² ...................................... A61F 13/00
[58] Field of Search ............ 128/132 D, 132 R, 292, 128/296

[56] References Cited
UNITED STATES PATENTS

| | | | |
|---|---|---|---|
| 2,715,902 | 8/1955 | Shaffer et al. | 128/132 D |
| 3,589,365 | 6/1971 | Seiman | 128/132 D |
| 3,625,205 | 12/1971 | Madden et al. | 128/132 D |
| 3,777,749 | 12/1973 | Collins et al. | 128/132 D |
| 3,889,667 | 6/1975 | Collins | 128/132 D |

FOREIGN PATENTS OR APPLICATIONS

| | | | |
|---|---|---|---|
| 453,572 | 6/1968 | Switzerland | 128/132 D |

Primary Examiner—Lawrence W. Trapp

[57] ABSTRACT

A surgical drape of the invention has a main sheet with a cuff at the top end thereof. The cuff is secured to the upper surface of the main sheet along lines of attachment that are placed inwardly a substantial distance from the side edges of the main sheet to provide a hand receiving pocket in the drape. A strip of adhesive is secured to the lower surface of the main sheet near the top edge of the drape and is protected, prior to use of the drape, by a removably adhered release sheet. The pocket in the drape receives the hands of a nurse who may easily and quickly secure the drape to the desired part of the patient's body by bringing the adhesive into contact with the patient and running her fingers back and forth over the adhesive strip lying under the pocket. The drape is particularly suited for application to the patient's head, especially the forehead, and hence is of particular utility in surgery involving the eyes, ears, nose or throat.

The drape is folded longitudinally and traversely into a compact unit which can be easily and quickly unfolded and applied to the patient. In its folded form, the drape compises two outwardly facing major surfaces on each of which is located a portion of the hand receiving pocket. The adhesive strip also faces outwardly on the completely folded drape. Thus the release sheet may be conveniently removed from the adhesive, and the hands inserted into the pocket portions, before the drape is unfolded from its folded form and applied to the patient.

11 Claims, 17 Drawing Figures

FOLDED SURGICAL DRAPE

This invention relates to surgical drapes and particularly to surgical drapes which are useful for covering a patient's head, or portions thereof, especially during surgery on the eyes, ears, nose and throat.

During surgery involving the eye, ears, nose and throat, it is necessary to drape the patient's head in order to isolate the operative area and also to cover the patient's hair.

One method for draping a patient's head involves the use of two operating room towels and towel clips and requires the cooperation of two operating room nurses. A patient about to undergo a tonsillectomy, for example, is draped as follows. One nurse lifts the patient's head. A second nurse, after first placing one towel on top of the other, places the two towels, in more or less centered position, beneath the patient's head which is then lowered to lie on top of the towels. The ends of the upper towel are then brought upwardly around the sides of the head to a position overlying the forehead and are then secured together, in turban-like fashion, with the aid of one or more towel clamps. The lower towel remains in position between the patient's head and operating room table.

This draping technique is disadvantageous in several respects. First of all, the draping technique involves two nurses. Secondly, since ends of the towel are joined together in the forehead region with towel clips, the latter frequently are in the way when the surgery is subsequently performed. Another disadvantage is that the towel used to drape the head may be torn or otherwise damaged by using towel clips to secure the ends of the drape.

In accordance with the present invention, there is provided a surgical drape which overcomes the above mentioned disadvantages. The drape of this invention may be applied quickly and easily, and in an aseptic fashion, by one nurse, and towel clips, or securing devices of like nature, are not needed. One of the two nurses needed to help drape the patient according to former methods is released to attend to other duties, thus reducing the time required in preparation for surgery. There are no towel clips to interfere with the surgeon or his assistants during the operation, and tearing or other damage to the drape is avoided.

These and other advantages are obtained by providing a surgical drape comprising a main sheet of flexible drapable material having a cuff at one end thereof. The cuff is located on the upper surface of the main sheet and has a pocket associated therewith for receiving the hands of a surgeon or nurse. The bottom or lower surface of the drape carries a strip of adhesive by means of which the drape may be secured in a desired position to a portion of a patient's body, e.g., the head. The strip of adhesive is protected prior to use by a removably adhered protective covering referred to hereinafter as a "release sheet" or a "release strip".

In a preferred embodiment of the present invention, at least a central portion of the cuff of the drape has a reinforcing panel secured thereto, which reinforcing panel provides a double thickness of material which resists tearing and abrasive forces to which the drape may be subjected during use. The reinforcing panel is preferably secured to the upper surface of the cuff. Even more preferably the reinforcing panel comprises a liquid impervious layer having a liquid absorbent upper surface, the reinforcing panel being secured, e.g., with an adhesive so that its upper abosrbent surface constitutes part of the upper surface of the drape.

In accordance with a further aspect of the present invention, the drape is folded into a compact unit which can be safely held in one hand and so that the release covering on the pressure sensitive adhesive may be easily removed with the other hand, after which the drape may be readily unfolded and quickly and aseptically applied to the patient.

The term "upper surface" as used herein refers to a surface which faces away from the patient when the drape is in use. The term "lower surface" refers to a surface which faces the patient when the drape is in use. BRIEF DESCRIPTION OF THE DRAWINGS

DESCRIPTION OF THE PREFERRED EMBODIMENT

Referring now to FIGS. 1–5, there is shown one embodiment of the surgical drape of the present invention. Drape 20 is generally rectangular in shape and comprises a main sheet 22 having a top edge 24, a bottom edge 25 and opposed side edges 26 and 27. The main sheet has an upper surface 30 and a lower surface 31. The top, bottom, and opposed side edges of main sheet 22 define the top, bottom and opposed side edges, respectively, of drape 20. The main sheet has a top portion 40 adjacent its top edge, a bottom portion 42 adjacent its bottom edge, and a generally centrally located intermediate portion 41 between its top and bottom portions.

The main sheet may be made from any woven, nonwoven, or plastic material. Preferably, however, the main sheet comprises a flexible, drapable nonwoven fabric and, more preferably, the nonwoven fabric is liquid repellent to prevent strike-through of liquids, such as water, blood and the like, which are normally encountered during surgery.

The drape further comprises a cuff comprises a cuff portion 32 which overlies the upper surface of top portion 40 at the top end of the main sheet. Cuff 32 has a top edge 34, a bottom edge 35, and opposed side edges 36 and 37. In the preferred embodiment under discussion, cuff 32 is integral with main sheet 22, top edge 34 of the cuff coinciding with top edge 24 of the main sheet to form the top edge of the drape. In the illustrated embodiment the cuff is of the same width as the main sheet, edges 36, 37 of the cuff being in substantial alignment with edges 26, 27 of the main sheet, respectively. Bottom edge 35 of the cuff is generally parallel to, and lies between, the top and bottom edges of the main sheet. The depth of the cuff, that is, the distance along its side edges 36, 37, may vary from about 6 inches to about 14 inches; preferably cuff 32 is about 10 inches deep.

Figures 3, 4:
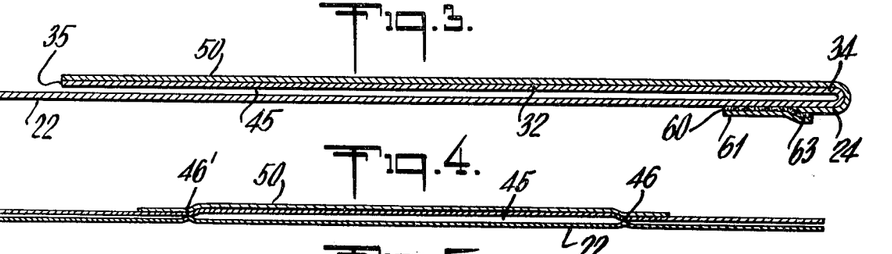
FIG. 3 is an enlarged cross-sectional view taken along lines 3—3 0f FIG. 1.
FIG. 4 is an enlarged cross-sectional view taken along lines 4—4 of FIG. 1.

Cuff 32 may be made from any of the materials mentioned earlier for main sheet 22, and preferably the cuff and main sheet are made from the same material. It will be recognized that the main sheet and cuff could be separate pieces of material attached, e.g., by stitching, along a line adjacent their coinciding upper edges. Preferably, as shown in FIG. 3, the main sheet and cuff comprise a single piece of nonwoven fabric, the cuff being formed by suitably folding back a portion of the nonwoven fabric upon itself.

Figure 1:
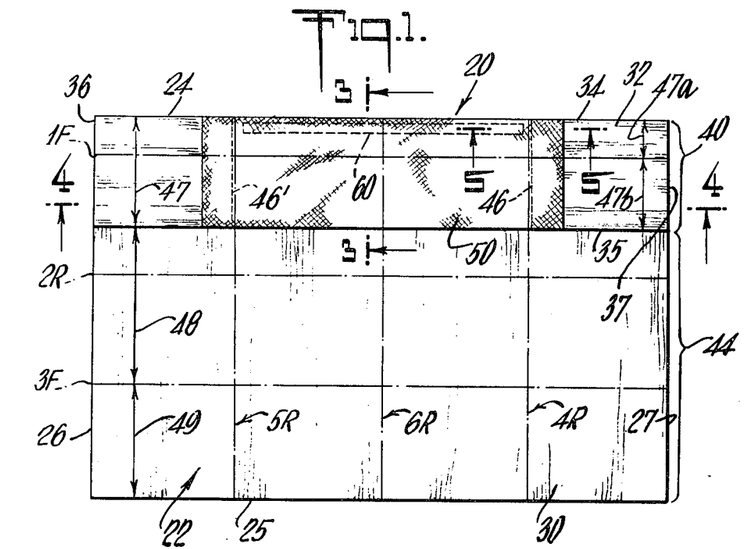
FIG. 1 is a top plan view of one embodiment of a surgical drape in accordance with the present invention, and showing the fold lines for folding the drape in the longitudinal direction.

Referring to the upper right hand side of FIG. 1, it will be seen that the drape comprises an upper portion 47, an intermediate portion 48, and a bottom portion 49. Upper portion 47 of the drape, which includes top portion 40 of the main sheet and overlying cuff 32, comprises an upper part 47a and a lower part 47b. Upper part 47a lies adjacent the upper edge of the drape, and has its upper and lower edges defined by the upper edge of the drape and fold line 1F, respectively. Lower part 47b of the upper portion of the drape lies adjacent upper part 47b and has its upper edge defined by fold line 1F. Its lower edge is defined by the lower edge of cuff 32 (in the case where cuff 32 has the same width as the main sheet) or by a line coinciding with the lower edge of cuff 32 and extending from one side of the drape to the other (in the case where cuff 32 is not as wide as the main sheet).

Intermediate portion 48 of the drape corresponds to intermediate portion 41 of the main sheet. Bottom portion 49 of the drape lies adjacent the bottom edge of the drape and corresponds to bottom portion 42 of the main sheet.

The remainder portion 44 of the drape comprises intermediate portion 48 and bottom portion 49.

The drape has a hand receiving portion or pocket 45 located between cuff 32 and upper portion 40 of the main sheet. Although this pocket may comprise a separate envelope of material secured, e.g., with stitching to the underside of cuff 32, pocket 45 is preferably and most conveniently formed by securing the cuff to the upper surface of top portion 40 of the main sheet along generally longitudinally extending, spaced lines of attachment 46, 46'. These lines of attachment are preferably parallel to side edges 36, 37 of the cuff, and hence are preferably perpendicular to the top edge of the drape and the bottom edge of the cuff. The attachment of cuff 32 to main sheet 22 along lines 46, 46' is preferably accomplished with an adhesive, although other means such as stitching may be used if desired. Thus, it will be seen that pocket 45 has an upper edge defined by that portion of the upper edge of the drape lying between lines of attachment 46, 46'; a lower edge defined by that portion of the lower edge of the cuff lying between lines 46, 46'; and opposed side edges defined by lines of attachment 46, 46'. That portion of bottom edge 35 of the cuff lying between the lines of attachment of substantially free of attachment to the main sheet. In the preferred embodiment, then, pocket 45 is closed at its upper and side edges and is open at the lower edge of the cuff, that is, pocket 45 opens away from the top edge of the drape. It will be recognized that the gluing or stitching along lines 46, 46' may be either intermittent or continuous, the latter being preferred. Similarly, if separate pieces of material are used for the main sheet and the cuff, these could be joined together along their upper edges by either an intermittent or continuous glue line or stitch line.

The lines of attachment 46, 46' are spaced inwardly a substantial distance from side edges 26, 27 respectively of the main sheet. The drape should be wide enough to cover the patient and extend at least to, and preferably somewhat beyond, the sides of the operating table. As rule of thumb, where the drape will be used for surgery on the eyes, nose, or throat, the drape should be around 50 inches wide although it will be recognized that this dimension could vary. The pocket in the drape must have a width that is considerably smaller than the width of the drape itself. As will be seen, the pocket receives the nurse's hands during application of the drape. As the width of the pocket increases, the nurse's hands will be free to move further and further apart before they reach the sides of the pocket, and she will find it increasingly difficult to control the drape while it is being unfolded and applied to the patient. It will be understood that the pocket should be at least wide enough to accept two hands in side by side relationship. Furthermore, if the pocket is overly wide, the nurse's control over adhesive strip 60 is greatly reduced, thus making it difficult to line up the adhesive strip and press it into contact with the patient's body.

Preferably, the width of the pocket (that is, the distance between lines of attachment 46, 46') is from about 1/3 to about 2/3 of the width of the drape (that is, the distance between opposed side edges 26 and 27 and of the main sheet). Most preferably with width of the pocket is about ½ of the width of the drape itself.

Although in the illustrated embodiment, the width of the cuff is substantially the same as the width of the main sheet, it will be understood that the width of the cuff may be less than the width of the main sheet. Cuff 32 need be only as wide as the width of the main sheet. Cuff 32 need be only as wide as the width selected for pocket 45 which is formed in the drape by securing the cuff to the main sheet along lines of attachment 46, 46'. Stated otherwise, it will be recognized that the side portions of the cuff shown in the FIG. 1 (i.e., the portion between line 46 and edge 37 and the portion between line 46' and edge 36) are not essential to the structure of the drape. These side portions are there as a result of the fact that, in the preferred embodiment, the main sheet and cuff are made from a single piece of nonwoven fabric. The portions referred to, of course, could be cut away without any effect whatsoever on the essential structural features of the drape, but this would only increase the time necessary to fabricate the drape and no benefit would be gained thereby.

Figures 2, 5:
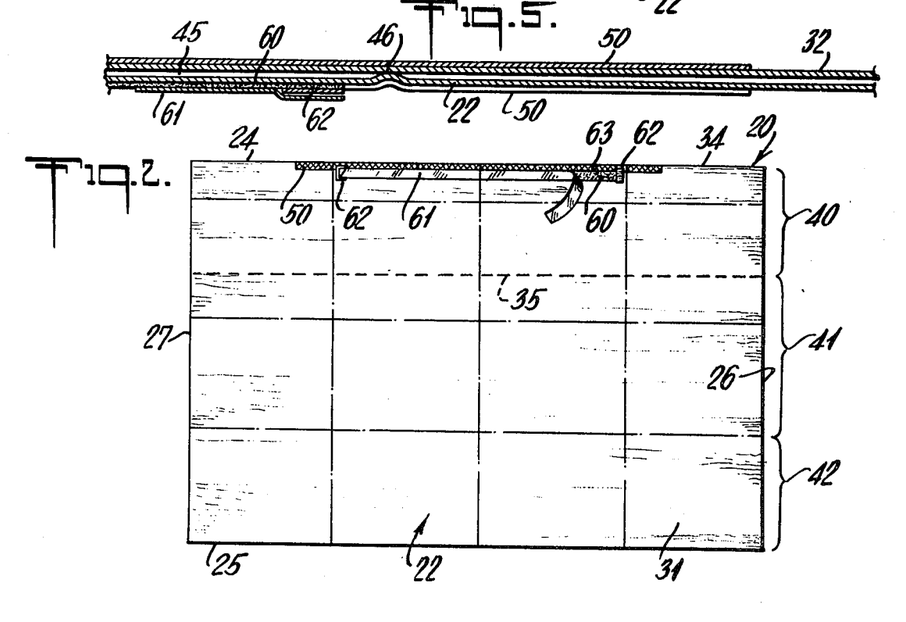
FIG. 2 is a bottom view, with portions turned back, of the drape of FIG. 1.
FIG. 5 is an enlarged cross-sectional view taken along lines 5—5 of FIG. 1.

In a particular embodiment that has been judged to be satisfactory to draping an average sized person lying on a standard operating table, the width of the drape is 50 inches and the width of pocket 45 is about 26 inches. Line of attachment 46' is about 12 inches from side edge 26 of the main sheet and line of attachment 46 is about 12 inches from side edge 26. Thus pocket 45 formed in cuff 32 lies inwardly of the sides of the drape. Preferably the pocket is located symmetrically, that is, the distance between line 46' and side edge 26 is equal to the distance between line 46 and side edge 27. The length of the drape may be varied depending upon the type of surgical procedure with which it will be used. A drape whose length is about 40–48 inches has been found useful for a variety of surgical procedures. Preferably, as seen in the figures, the drape further comprises a reinforcing panel 50 attached to a portion of the upper surface of cuff 32. The reinforcing panel may comprise any suitable woven, nonwoven, or plastic material, e.g., the reinforcing panel could be the same material as that used for the main sheet. Preferably the reinforcing panel comprises a liquid impervious layer, such as a plastic film having a liquid absorbent upper surface. This reinforcing panel is secured to the upper surface of cuff 32 so that its liquid absorbent upper surface comprises part of the upper surface of the drape. The absorbent surface of the reinforcing panel absorbs liquids such as water and blood, and the underlying liquid impervious layer thereof prevents such liquids from striking through to cuff 32 and/or main sheet 22. The reinforcing panel is most suitably secured to the cuff by an adhesive. Preferably, as seen in FIGS. 2 and 3, the reinforcing panel is folded over the upper edge of the drape (i.e., over edge 24 of the main sheet and edge 34 of the cuff) and continued a short distance, e.g., ½ – ¾ inch, along the bottom surface of the main sheet. This construction "rounds off" and reinforces the upper edge of the drape. In the embodiment illustrated in FIG. 1, the reinforcing panel is wide enough to extend somewhat beyond lines 46, 46', and is long enough to cover the cuff from its top to its bottom edges. The dimensions of the reinforcing panel may be varied if desired, buy preferably the reinforcing panel is of sufficient size to cover the upper surface of the cuff in the region thereof which overlies pocket 45.

Referring now to FIG. 2, it will be seen that drape 20 also comprises strip of adhesive 60 adhered to the bottom surface of upper part 47a of the drape and adjacent the top edge of the drape. In the embodiment under discussion, part of adhesive strip 60 is adhered to and covers a portion of reinforcing panel 50 that has been folded over the upper edge of the drape and secured to the lower surface of main sheet 22. It will be understood that the adhesive strip may also be placed on the bottom surface of the main sheet adjacent the edge of the reinforcing panel or part of the adhesive strip could be placed under the portion of the reinforcing panel secured to the bottom side of the drape. In the latter case, that portion of the adhesive covered by the reinforcing panel would, of course, be unavailable for securing the drape to the patient. In any event, it will be recognized that, since it is desired to adhesively secure the drape to a patient, there must be a strip of adhesive exposed on the bottom of the drape to acheive this purpose. The length and width of the adhesive strip may be varied, preferably, the adhesive strip is long enough to extend substantially from one side of pocket 45 to the other.

Adhesive 60 is protected prior to use with a releasably adhered protective covering, or release sheet 61. As seen in FIG. 2, a small piece 62 of release sheet is placed on the adhesive at one end thereof so that it lies between the adhesive and a small end portion 61 of release sheet 60. The presence of release sheet 62 prevents the small end portion of release sheet 60 from adhering to the portion of adhesive 60 directly beneath it. Thus there is no difficulty in separating release sheet 61 from adhesive 60 prior to applying the drape to the patient.

As illustrated in the Figures, the length of adhesive strip 60 corresponds approximately to the width of hand receiving pocket 45. The width of the adhesive strip may be varied, but a width of about 1 inch has been found quite suitable. The upper edge 63 of the adhesive strip may coincide with the upper edges of the cuff and the main sheet; preferably, however, the upper edge of the adhesive is spaced inwardly a short distance (e.g., ½ inch) from the upper edge of the drape.

As mentioned, adhesive 60 is used to attach the drape to a patient about to undergo surgery. Any of the adhesives well known in the art for this purpose may be used, the only requirements being that the adhesive be non-toxic, stable to ordinary sterilization procedures, and removably adherable to the body surface to which it will be applied.

FOLDING OF THE DRAPE

In accordance with another aspect of the present invention, the surgical drape is folded longitudinally and transversely into a compactly folded unit. The folded drape is easily inserted into, and sealed within, a suitable container such as a paper bag. The packaged, folded drape may be sterilized with steam, ethylene oxidize or radiation. Advantageously, the sterilized folded drape of the present invention may be quickly unfolded and easily applied to the patient by one nurse.

The folding of drape 20 will be described with reference to FIG. 1 and FIGS. 6–11 of the drawings.

As used herein a "forward fold" is a fold in which the upper surface is turned toward the upper surface of the drape around a fold line. A "reverse fold" is a fold in which the upper surface of the drape is turned toward the bottom surface of the drape around a fold line. In the drawings, the letter R indicates a reverse fold and the letter F indicates a forward fold. The numbers preceding the letters F and R refer to the order in which the folding is done.

The drape is folded at least two times from its top edge toward its bottom edge to give a longitudinally folded drape which is reduced in length and wherein the adhesive (and its release sheet) is exposed on the upper surface of the folded drape. The size of the folds may vary but it is required, after the longitudinal folding is completed, that the adhesive be available on the upper major surface of the longitudinally folded drape and that the location of the opening into pocket 45 be ascertainable by the nurse or other person who will be unfolding the drape and applying it to the patient.

In order to achieve the above objectives the first fold must be a forward fold around the transversely extending fold line along which the upper part of the upper portion of the drape joins the bottom part of the upper portion of the drape. The second fold must be a reverse fold around a tansversely extending fold line which runs from side to side of the drape in the remainder portion of the drape, i.e., in either the intemediate portion or bottom portion.

The longitudinally folded drape may be folded transversely to provide a compactly folded drape that is reduced in size and readily packaged. The transverse folding must be such that pocket 45, or at least a portion thereof, is available on an outer major surface of the completely folded drape. Also, when the transverse folding is completed, adhesive 60 and release sheet 61 must be exposed outwardly so that the peel strip can be removed before the drape is unfolded.

Figures 6, 7, 8, 9, 10, 11:
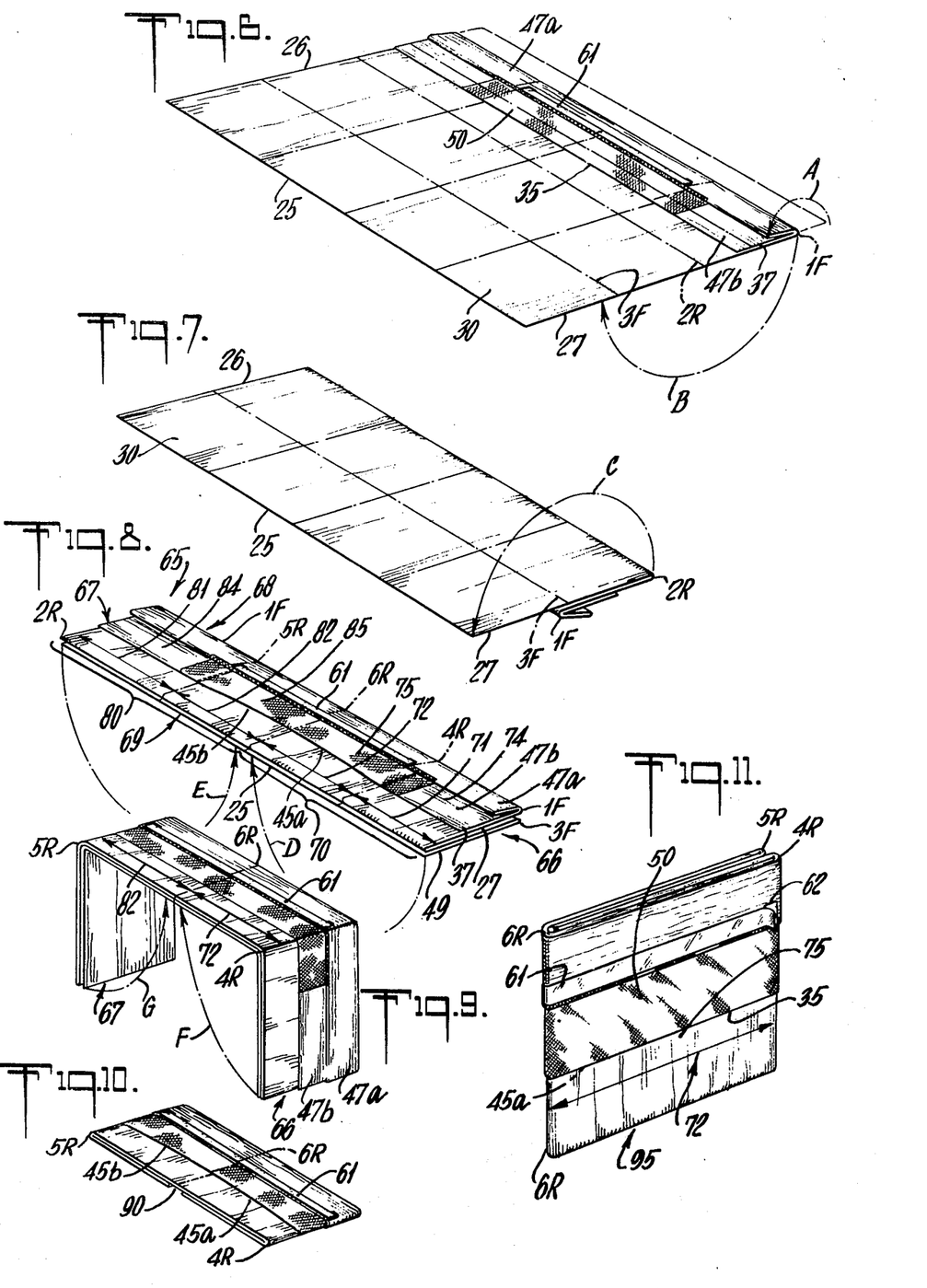
FIG. 6 is a perspective view of the drape of FIG. 1 after the first longitudinal fold is made.
FIG. 7 is a perspective showing an intermediate stage of the longitudinal folding.
FIG. 8 is a perspective of the drape after the longitudinal folding has been completed and showing the fold lines for the transverse folding of the drape.
FIG. 9 is a perspective showing the initial steps in the transverse folding sequence.
FIG. 10 is a perspective showing the drape in flat form after the first stage of the transverse folding has been completed.
FIG. 11 is a perspective showing the drape completely folded.

The preferred method for folding drape 20 in the longitudinal direction, that is, from top to bottom, is illustrated in FIGS. 1 and 6–8. The drape is folded three times in the longitudinal direction. Referring particularly to FIG. 6, upper part 47a of the upper portion of the drape is forward folded around fold line 1F (Arrow A in FIG. 6). As a result of this folding step, upper part 47a lies on top of lower part 47b of upper portion 47 of the drape. Adhesive strip 60 (protected by release sheet 61) then overlies the upper surface of the drape, the original top edge of the drape now lying between fold line 1F and bottom edge 35 of the cuff.

The length, that is, the distance along the side edges of the drape, of upper part 47a must not be more than half the length of cuff 32. Another way of saying this is that the length of upper part 47a must not exceed the length of lower part 47b. As long as the length of upper part 47a is so restricted, the original upper edge of the drape will either lie somewhere between fold line 1F and bottom edge 35 of the cuff or will coincide with bottom edge 35, after the fold has been made around fold line 1F. Adhesive strip 60 faces upwardly and the location of hand receiving pocket 45 is readily ascertainable inasmuch as bottom edge 35 of the cuff—which defines the open end of pocket 45—is still exposed to view. On the other hand, when the length of upper part 47a exceeds half the length of cuff 32, then (when the fold around 1F is completed) upper part 47a will cover bottom edge 35 of the cuff and conceal the location of the opening to pocket 45 from the nurse's view.

The preferred longitudinal folding is continued by reverse folding the drape around fold line 2R in the direction shown by arrow B in FIG. 6 to give the longitudinally folded configuration shown in FIG. 7. Fold line 2R extends transversely of the drape through intermediate portion 41 of the main sheet. Fold line is spaced a substantial distance, e.g., 2 to 3 inches, from edge 35 of cuff 32. It will be understood, however, that fold line 2R could substantially coincide with the edge of cuff 35, that is, the second fold could be made in reverse fashion around the transverse line along which intermediate portion 41 joins upper portion 40 of the main sheet. This latter mentioned placement of fold line 2R would be somewhat disadvantageous, since as will be seen, edge 35 of the cuff, and therefore the opening into pocket 45, would be at the bottom edge of the drape after the third longitudinal fold is made. Thus, it would be difficult, in applying the drape, for the nurse to quickly and easily locate the pocket into which she must insert her hands.

The preferred longitudinal folding is completed by forward folding the drape around fold line 3F in the direction indicated by arrow C in FIG. 7. Fold line 3F extends transversely of the drape and corresponds to the transverse line along which the intermediate portion of the main sheet joins the bottom portion of the main sheet.

FIG. 8 shows the drape after it has been folded longitudinally in the manner just described. In FIG. 8, the portion of cuff edge 35 between lines 46, 46' has been "raised" somewhat to more clearly illustrate pocket 45. It will be noted that adhesive 60 (with its protective covering 61) is on the upper surface of the longitudinally folded drape 65. Bottom edge 35 of the cuff is easily viewable thus allowing the opening into pocket 45 to be readily located. The lower edge 35 of the cuff lies between upper edge 68 and lower edge 69 of longitudinally folded drape 65, and upper part 47a of the drape overlies lower part 40b. After the above described longitudinal folding sequence has been completed, the longitudinally folded drape comprises 3 folds overlying the upper surface of bottom portion 49 of the drape (See FIG. 8).

The longitudinally folded drape shown in FIG. 8 may be folded transversely a number of times to provide a completely folded drape in the form of a relatively small, compact unit. The transverse folding can be accomplished in a number of ways providing that at least a portion of pocket 45 is available on an outer major surface of the transversely folded drape. Preferably the drape is folded transversely so as to provide a portion of pocket 45 on each major surface of the completely folded drape.

It has been found extremely advantageous, from the point of view of handling and applying the drape, to divide the longitudinally folded drape into transverse portions and fold the drape so that portions of pocket 45 are made available on the outwardly facing major surfaces of the drape after it has been completely folded. Preferably, the drape is folded so that pocket 45 is divided into 2 portions and there is one such divided pocket portion on either side of the drape after it has been completely folded in the transverse direction.

The preferred transverse folding of the drape will now be illustrated with reference to FIGS. 8–11 of the drawings.

As shown in FIG. 8, longitudinally folded drape unit 65 comprises a first transverse portion 70 and a second transverse portion 80 which adjoin each other along longitudinally extending fold line 6R. First transverse portion 70 comprises an outer portion 71 and an inner portion 72 which adjoin each other along longitudinally extending fold line 4R; similarly, second transverse portion 80 comprises an outer portion 81 and an inner portion 82 which adjoin each other along longitudinally extending fold line 5R. Outer portion 71 lies between right side edge 66 of longitudinally folded drape 65 and fold line 4R, while inner portion 72 lies between fold lines 6R and 4R. Outer portion 81 lies between left side edge 67 of the longitudinally folded drape 65 and longitudinally extending fold line 5R, while inner portion 82 lies between fold lines 6R and 5R. In the preferred folding, fold line 4R substantially coincides with line of attachment 46 and fold line 5R substantially coincides with line of attachment 46' (see upper portion of FIG. 1).

In the preferred embodiment, portions 70 and 80 are of substantially equal size. Portion 71 is substantially the same size as portion 81, and portion 72 is substantially the same size as portion 82. For reasons that will appear hereinafter, it is preferred that the width of outer portion 71 (that is, the distance from fold line 4R to outer edge 66) be smaller than the width of portion 72 (that is, the distance from fold line 4R to fold line 6R). Similarly, the width of outer portion 81 is preferably somewhat smaller than the width of portion 82. It will be understood, however, that the above mentioned sizes of portions 70 and 80, and of portions 71, 72 and 81 and 82 are preferred, not critical. The dimensions of the several portions may be changed to suit various needs. As will be seen hereinafter, the essential thing is that when the transverse folding is completed, there be a portion of pocket 45 on each outwardly facing major surface of the folded drape, each pocket portion being of sufficient size to receive a person's hand.

The preferred transverse folding of the longitudinally folded drape 65 is accomplished as follows: First transverse portion 70 is folded backwardly back upon itself by reverse folding outer portion 71 thereof around fold line 4R so that the lower surface of outer portion 71 comes into face to face contact with the lower surface of inner portion 72. This is indicated by arrow D in FIG. 8. Second transverse portion 80 is folded backwardly upon itself by reverse folding outer portion 81 thereof around fold line 5R so that the bottom surface of outer portion 81 comes into face to face contact with the bottom surface of inner portion 82. This is indicated by arrow E in FIG. 8.

When, as is preferred, portions 71 and 81 are selected to have widths somewhat smaller than the widths of portions 72 and 82, respectively, edges 66 and 67 will lie one on either side of fold line 6R, and with a slight separation 90 between them, when the drape is in the folded condition illustrated in FIG. 10. As shown in FIG. 10, separation 90 lies beneath fold line 6R. Thus, as will be seen, when the transverse folding is completed, there will be no bulges in the final folded unit and there will be no additional undesirable folds imparted to portions 71 or 81.

The transverse folding is completed by folding folded transverse portion 70 backwardly around longitudinally extending fold line 6R toward folded transverse portion 80. This brings upper surface 74 of outer portion 71 into face-to-face contact with upper surface 84 of outer portion 81. Upper surface 75 of inner portion 72 then comprises one of the outwardly facing major surfaces of the completely folded drape 95, while outer surface 85 of inner portion 82 comprises the other outwardly facing major surface of the drape. Completely folded drape 95 is shown in FIG. 11. A portion 45a of pocket 45 is on the outer major surface seen by the viewer in FIG. 11. Portion 45b of pocket 45 is on the opposite major surface of drape 95 shown in FIG. 11.

APPLICATION OF THE DRAPE TO THE PATIENT

The manner of applying the drape to a patient about to undergo, e.g., eye surgery, will now be explained with reference to FIGS. 12–27.

Figure 12:
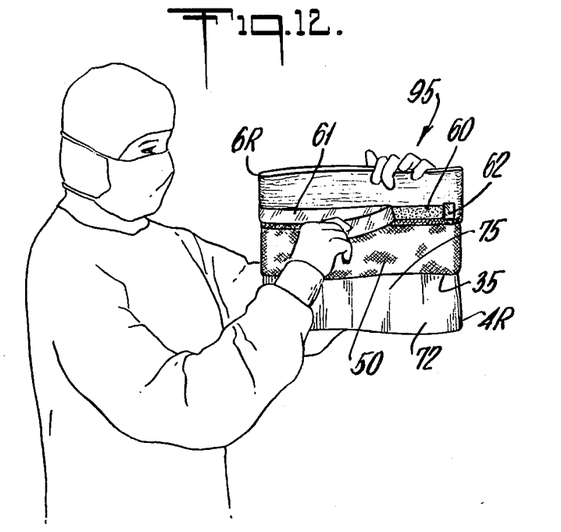
FIG. 12 is a perspective of the nurse holding the folded drape of FIG. 11 in her left hand and starting to remove the release paper from the adhesive with her right hand.
Figure 13:
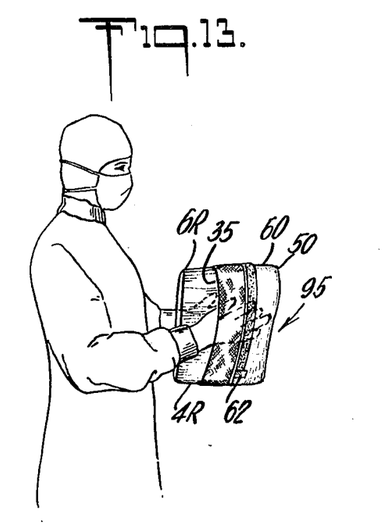
FIG. 13 is a perspective showing the nurse's hands, with palms facing each other, inserted into the pocket portions on each major surface of the completely folded drape.
Figures 14, 15, 16, 17:
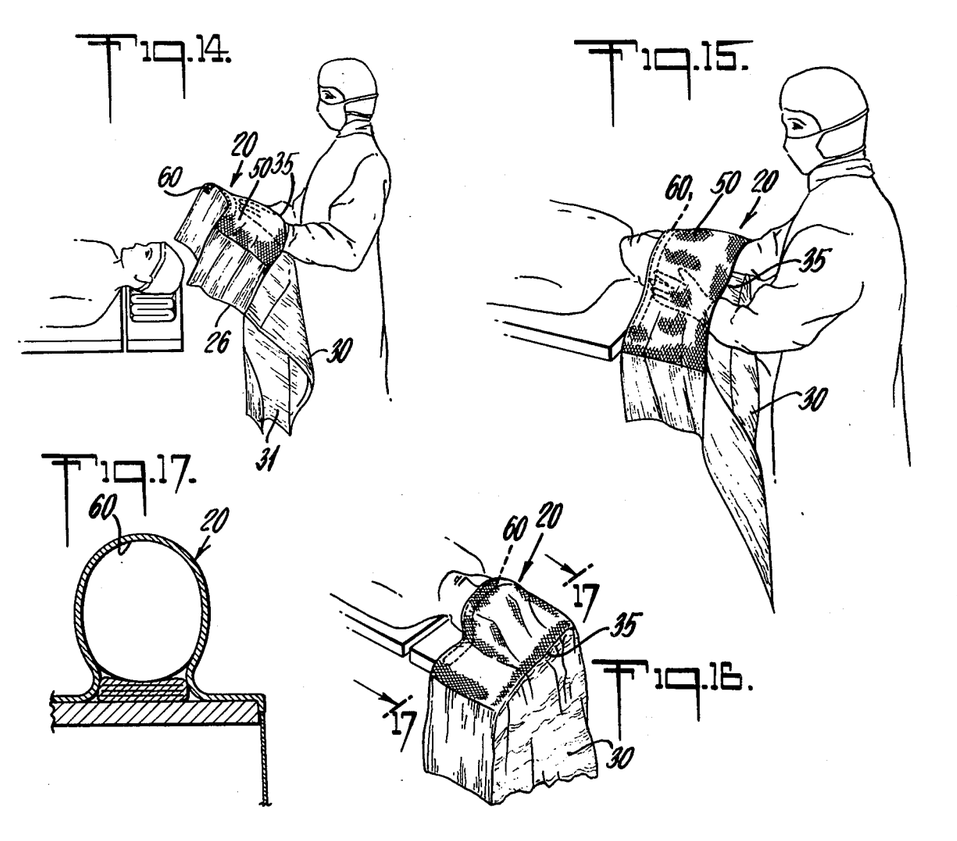
FIG. 14 is a perspective showing the drape in its unfolded condition and the nurse about to apply the drape to a patient's head.
FIG. 15 is a perspective showing the drape secured to a patient's forehead, the nurse's hands now being in a "palms-down" position within the hand-receiving pocket of the drape.
FIG. 16 is a perspective showing the drape after it has been fully applied to the patient.
FIG. 17 is a cross-sectional view taken along lines 17—17 of FIG. 26.

FIG. 12 shows a nurse holding the surgical drape of the present invention in her left hand and removing peel strip 61 from pressure sensitive adhesive 60 with her right hand. It will be understood that the drape in FIG. 12 has been folded in the manner described earlier herein and as illustrated in FIGS. 6–11. After the peel strip has been removed from the underlying adhesive, the nurse inserts her right hand into pocket portion 45a (that pocket on the major surface of folded drape 95 facing the viewer in FIG. 12) and her left hand into pocket portion 45b (that pocket on the major surface of the drape not facing the viewer in FIG. 12). The resulting position of the nurse's hands in the pockets on either side of the folded drape is illustrated in FIG. 13. It will be noticed that the hands are inserted into the pockets so that the fingers point toward top edge of the folded drape, said top edge being defined by fold line 1F. The thumbs are pointing generally toward the closed side of the folded drape, that is, they are pointing generally toward fold line 6R. Starting from the position of FIG. 13, the nurse moves her hands to a "palms down" position, then spreads her arms outwardly thus allowing the transverse folds of the drape to unfold. At the same time, the nurse moves her right hand toward, then against, the right side edge of pocket 45, that is, toward and against line of attachment 46, and her left hand toward, then against, the left side edge of pocket 45, that is toward line of attachment 46'. The nurse, at the same time, uses her hands, and especially the tips of her fingers, to "slip over" and unfold portion 47a. When this has been done, the drape is completely unfolded and adhesive 60 on portion 40 is returned to its position on the underside of the drape and facing the patient. (See FIG. 14.) It will be observed that the nurse's hands, since they are within the pocket during the unfolding and application of the drape, are protected from accidental contact with a non-sterile surface, such as, for example, an item of operating room equipment or the patient's hair. The nurse then brings the center portion of adhesive 60 into contact with the patient's forehead, thereby securing the drape to the patient as shown in FIG. 15. The nurse then uses her hands, which are still within pocket 45, to adjust the position of the drape and press the adhesive into contact with the desired parts of the patient's body. FIG. 16 shows the drape in position on the patient's head so that the hair and ears are covered. FIG. 17 is a schematic cross-section illustrating how the drape can be tucked in toward the patient's neck to further increase the coverage provided by the drape. Also, as seen in FIG. 16, if strip 60 of adhesive has been made sufficiently long, the ends thereof may be used to also secure the drape to the operating table.

Those skilled in the art will recognize that various changes and modifications can be made in the preferred embodiments described herein without departing from the spirit and scope of the present invention.

What is claimed is:

1. A surgical drape comprising:
   a. a main sheet of flexible, drapable material, said main sheet having an upper surface and a lower surface, a top edge, a bottom edge, and opposed side edges, an upper portion adjacent said top edge and a remainder portion adjoining said upper portion; said upper portion comprising a top part and a bottom part, said top part of said upper portion being not larger than said bottom part of said upper portion, said top part joining said bottom part along a first line running transversely of said main sheet;

b. a cuff overlying the upper surface of said upper portion of said main sheet, said cuff having a top edge, a bottom edge, and opposed side edges, said cuff being integral with said main sheet along the respective top edges of said cuff and said main sheet, said cuff being further secured to the upper surface of said main sheet along generally longitudinally extending lines of attachment which are spaced inwardly a substantial distance from the side edges of said main sheet, whereby, after said cuff has been attached to said main sheet along said lines of attachment, a hand receiving pocket is provided in said drape; and c. a strip of adhesive for removably adhering the drape to the body of a patient, said strip of adhesive being secured to the lower surface of the top part of the upper portion of said main sheet, said drape being folded longitudinally at least two times, the first fold being made by forward folding said top part around said first transverse line; the second fold being made by reverse folding the drape around a line extending transversely of the drape and through said remainder portion whereby, when the folding is completed, a longitudinally folded drape is provided which is reduced in length and wherein said adhesive is exposed on the upper surface of the folded drape.

2. A folded surgical drape according to claim 1 further folded in the transverse direction to provide a compactly folded drape.

3. A surgical drape comprising:

a. a main sheet of flexible, drapable material, said main sheet having an upper surface and a lower surface, a top edge, a bottom edge and opposed side edges, an upper portion adjacent said top edge, a lower portion adjacent said bottom edge and an intermediate portion between said upper portion and said lower portion; said upper portion comprising a top part and a bottom part, said top part of said upper portion being not larger than said bottom part of said upper portion, said top part joining said bottom part along a first line running transversely of said main sheet; said intermediate portion joining said bottom portion along a second line running transversely of said main sheet;

b. a cuff overlying the upper surface of said upper portion of said main sheet, said cuff having a top edge, a bottom edge, and opposed side edges, said cuff being integral with said main sheet along the respective top edges of said cuff and said main sheet, said cuff being further secured to the upper surface of said main sheet along generally longitudinally extending lines of attachment which are spaced inwardly a substantial distance from the side edges of said main sheet, whereby, after said cuff has been attached to said main sheet along said lines of attachment, a hand receiving pocket is provided in said drape; and c. a strip of adhesive for removably adhering the drape to the body of a patient, said strip of adhesive being secured to the lower surface of the top part of the upper portion of said main sheet.

said drape being folded longitudinally at least three times, the first fold being made by forward folding said top part around said first transverse line; said second fold being made by reverse folding the drape around a line extending transversely of the drape and through said intermediate portion; the last fold being made by forward folding the drape around said second transverse line whereby, when the folding is completed, a longitudinally folded drape is provided which comprises a plurality of folds overlying said bottom portion, said adhesive strip being exposed on the upper surface of said folded drape.

4. A surgical drape according to claim 3 wherein the drape is folded three times.

5. A longitudinally folded surgical drape according to claim 4, said longitudinally folded surgical drape comprising a first transverse portion and a second transverse portion, said transverse portions joining each other along a first longitudinally extending fold line; said first transverse portion comprising an inner portion and an outer portion joining each other along a second longitudinally extending fold line and said second transverse portion comprising an inner portion and an outer portion joining each other along a third longitudinally extending fold line; the outer portion of said first transverse portion being reverse folded around said second longitudinally extending fold line and the outer portion of said second transverse portion being reverse folded around said third longitudinally extending fold line; one of said folded first and second transverse portions then being reverse folded around said first longitudinally extending fold line to provide a compactly folded surgical drape.

6. A surgical drape according to claim 5 wherein said second longitudinally extending fold line and said third longitudinally extending fold line substantially coincide with said lines of attachment along which said cuff is secured to said main sheet.

7. A compactly folded surgical drape according to claim 6 wherein said main sheet and said cuff comprise a nonwoven fabric.

8. A compactly folded surgical drape according to claim 6 further comprising a reinforcing panel attached to the upper surface of said cuff in the region thereof which overlies said pocket.

9. A surgical drape according to claim 8 wherein said reinforcing panel comprises a liquid impervious layer having an absorbent upper surface.

10. A surgical drape according to claim 10 wherein the width of said pocket is from about ⅛ to about ⅝ of the width of said drape.

11. A surgical drape according to claim 10 sterilized and packaged in said sterile condition.

* * * * *

UNITED STATES PATENT AND TRADEMARK OFFICE
CERTIFICATE OF CORRECTION

PATENT NO. : 3,952,738
DATED : April 27, 1976
INVENTOR(S) : Krzewinski, Henrietta K.

It is certified that error appears in the above-identified patent and that said Letters Patent are hereby corrected as shown below:

In the Abstract, 2nd paragraph, 4th line, the word "compises" should read --- comprises ---.

In Column 1, Line 26, the word "and operating" should read --- and the operating ---.

In Column 2, Line 60, the word "Fig. 26" should read --- Fig. 16 ---.

In Column 3, Line 16, delete one occurrence of "comprises a cuff"

In Column 3, Line 53, the word "47b" should read --- 47a ---.

In Column 4, Line 21, the word "of substantially" should read --- is substantially ---.

In Column 4, Line 60, the word "27 and of" should read --- 27 of ---.

In Column 4, Line 60, the word "with width" should read --- the width ---.

In Column 4, Line 65, the word "cuff" should be deleted.

In Column 4, Line 66, the whole line should be deleted.

In Column 5, Line 15, the word "to" should read --- for ---.

In Column 5, Line 56, the word "buy" should read --- but ---.

In Column 6, Line 9, the word "acheive" should read --- achieve ---.

UNITED STATES PATENT AND TRADEMARK OFFICE
CERTIFICATE OF CORRECTION

PATENT NO. : 3,952,738
DATED : April 27, 1976
INVENTOR(S) : Krzewinski, Henrietta K.

It is certified that error appears in the above-identified patent and that said Letters Patent are hereby corrected as shown below:

In Column 7, Line 11, the word "tansversely" should read --- transversely ---.

In Column 7, Line 13, the word "intemediate" should read --- intermediate ---.

In Column 12, Line 54, the word "Claim 10" should read --- Claim 9 ---.

Signed and Sealed this

Second Day of November 1976

[SEAL]

Attest:

RUTH C. MASON
*Attesting Officer*

C. MARSHALL DANN
*Commissioner of Patents and Trademarks*